US005409125A

United States Patent [19]

Kimber et al.

[11] Patent Number: 5,409,125

[45] Date of Patent: Apr. 25, 1995

[54] UNIT DOSE CONTAINER

[75] Inventors: Michael B. Kimber, New South Wales, Australia; Anders T. Kers; Börje Jonsson, both of Södertälje, Sweden

[73] Assignee: Aktiebolaget Astra, Sweden

[21] Appl. No.: 161,984

[22] Filed: Dec. 3, 1993

Related U.S. Application Data

[63] Continuation of Ser. No. 859,507, Jul. 14, 1992, abandoned.

[30] Foreign Application Priority Data

Dec. 11, 1989 [AU] Australia ........................... 46152/89

[51] Int. Cl.[6] ........................ B65D 1/02; A61M 5/24; A61M 5/31

[52] U.S. Cl. ................................ 215/32; 215/DIG. 3; 604/87; 604/240; 604/241; 604/244; 222/107; 222/541

[58] Field of Search .................... 215/32, 256, DIG. 3, 215/33, 35; 604/244, 240, 241, 87; 222/107, 541

[56] References Cited

U.S. PATENT DOCUMENTS

| | | | |
|---|---|---|---|
| Re. 27,155 | 7/1971 | Hansen | 18/5 |
| 1,960,858 | 5/1934 | Strauch | 128/272 |
| 2,324,237 | 7/1943 | Reichel | 215/32 |
| 2,711,171 | 6/1955 | Dunnican | 604/241 |
| 2,724,384 | 11/1955 | Berthiot | 128/216 |
| 3,114,369 | 12/1963 | Hall | 125/216 |
| 3,187,966 | 6/1965 | Klygis | 222/541 |
| 3,204,835 | 9/1965 | Michel | 222/541 |
| 3,272,366 | 9/1966 | Ikeda | 215/32 X |
| 3,356,244 | 12/1967 | Witchell | 215/32 |
| 3,402,713 | 9/1968 | Senkowski et al. | 604/241 |
| 3,419,172 | 12/1968 | Lee | 215/32 |
| 3,509,879 | 5/1970 | Bathish et al. | 215/32 X |
| 3,578,037 | 5/1971 | Flynn | 141/2 |
| 3,597,793 | 8/1971 | Weiler et al. | 18/5 |
| 3,610,297 | 10/1971 | Raaf et al. | 141/27 |
| 3,667,638 | 6/1972 | Cambio, Jr. | 215/32 |
| 3,853,157 | 12/1974 | Madalo | 141/2 |
| 3,931,815 | 1/1976 | Takatsuki | 128/2 |
| 3,993,223 | 11/1976 | Welker et al. | 227/107 |
| 4,018,222 | 4/1977 | McAleer et al. | 128/216 |
| 4,022,206 | 5/1977 | Hilleman et al. | 128/216 |
| 4,046,145 | 9/1977 | Choksi et al. | 128/215 |
| 4,150,744 | 4/1979 | Fennimore | 206/205 |
| 4,170,994 | 10/1979 | Komatsu | 215/32 X |
| 4,176,153 | 11/1979 | Weiler et al. | 264/524 |
| 4,178,976 | 12/1979 | Weiler et al. | 150/0.5 |
| 4,207,990 | 1/1980 | Weiler et al. | 220/267 |
| 4,239,726 | 12/1980 | Weiler et al. | 264/525 |

(List continued on next page.)

FOREIGN PATENT DOCUMENTS

| | | |
|---|---|---|
| 149570 | 5/1951 | Australia . |
| 154830 | 5/1953 | Australia . |
| 556483 | 8/1983 | Australia . |
| 1114083 | 8/1983 | Australia . |
| 3597689 | 12/1989 | Australia . |
| 0126718 | 11/1984 | European Pat. Off. . |
| 0326391 | 8/1989 | European Pat. Off. . |
| 0361028 | 4/1990 | European Pat. Off. . |
| 0388360 | 9/1990 | European Pat. Off. . |
| 2533036 | 2/1977 | Germany . |
| 3202232 | 8/1983 | Germany . |
| 1485832 | 9/1977 | United Kingdom . |
| 8503433 | 8/1985 | WIPO . |

*Primary Examiner*—Allan N. Shoap
*Assistant Examiner*—Vanessa Caretto
*Attorney, Agent, or Firm*—White & Case

[57] ABSTRACT

A liquid containing thermoplastic unit dose container (1) which comprises a body portion (2), a neck portion (3) and an outlet opening (7) at the end of the neck portion (3) which is sealed by a non-resealable cap (4). The outside wall of the neck portion (3) comprises a thread engagement portion (8) which is located at or proximate the outermost edge of the neck portion (3) so that after removal of cap (4) thread engagement portion (8) is adapted to engage within an inwardly facing screw thread channel (14) at the end of a syringe. This enables sealing connection of the container (1) to the syringe so that liquid within container (1) may be directly transferred from the container (1) to the syringe.

20 Claims, 1 Drawing Sheet

U.S. PATENT DOCUMENTS

| | | | |
|---|---|---|---|
| 4,240,422 | 12/1980 | Hazen | 604/241 |
| 4,240,424 | 12/1980 | Akhavi | 604/241 |
| 4,244,409 | 1/1981 | Wilson et al. | 150/0.5 |
| 4,258,867 | 3/1981 | Weiler et al. | 222/507 |
| 4,298,045 | 11/1981 | Weiler et al. | 150/0.5 |
| 4,465,472 | 8/1984 | Urbaniak | 604/122 |
| 4,483,348 | 11/1984 | Sher | 128/743 |
| 4,548,601 | 10/1985 | Lary | 604/204 |
| 4,568,346 | 2/1986 | van Dijk | 604/414 |
| 4,620,638 | 11/1986 | Schmidt | 215/32 X |
| 4,643,309 | 2/1987 | Evers | 215/32 X |
| 4,703,610 | 11/1987 | Bach | 215/32 X |
| 4,747,501 | 5/1988 | Greaves | 215/32 X |
| 4,834,149 | 5/1989 | Fournier et al. | 141/1 |
| 4,921,137 | 5/1990 | Heijena | 222/541 X |
| 4,979,630 | 12/1990 | Rose et al. | 215/32 |
| 5,035,689 | 7/1991 | Schroeder . | |
| 5,071,413 | 12/1991 | Utterberg | 604/283 |

UNIT DOSE CONTAINER

This application is a continuation of application Ser. No. 07/859,507, filed Jul. 14, 1992, now abandoned.

This invention relates to a thermoplastic container suitable for use in holding and transferring injectable solutions to a syringe.

There are many different forms of syringe which are presently available for use by the medical professions. The most appropriate syringe design for any one situation depends largely on the particular circumstances of use, the nature of the solution being injected and the location of the intended injection.

One particular design difference between various syringes is the manner in which the open end is shaped to accommodate a hypodermic needle. The two most popular forms of needle fitting are the friction fit fitting (such as the luer slip fitting) and the combination of screw thread and friction engagement fitting (such as the luer lock fitting). Screw thread engagement fittings of interest in the context of the present invention are female fittings having an internal thread such as in the case of the luer lock fitting and all references to screw thread engagement fittings on syringes hereafter are references to female fittings. A screw thread engagement fitting is the fitting of preference where the circumstances of use indicate that there is some prospect of the needle becoming disengaged with the syringe body (e.g. epidural injections). This invention is particularly concerned with containers suitable for transferring injectable solutions to syringes having a screw thread engagement fitting.

BACKGROUND ART

In the past, the general practice of surgeons or other medical practioners using hypodermic syringes has been to transfer an injection solution to a syringe from a glass vial using a broad channelled needle attached to the syringe body. Following transfer, this broad channelled needle has been removed from the syringe and replaced with a narrower channelled hypodermic needle suitable for injecting the solution into the patient. It will be appreciated that this past practice has necessitated the use of a number of separate components. Furthermore, as solution transfer for injecting into humans requires scrupulous sterilizing of components, this previous practice has required separate sterilizing measures to be taken at each step.

To avoid the problems of such transfer, it has been previously proposed to provide ampoules or vials holding a single dose. These single dose vials have been adapted to fit like cartridges into a syringe body onto which can be fitted a hypodermic needle. Such unit dose vials are normally manufactured from glass and sealed with a rubber membrane and the vial is punctured by attaching to the syringe body a double sided needle.

An alternative arrangement is disclosed in Australian patent 556,483 where a unit dose container is described made from a thermoplastic material which is adapted to be opened and co-operatively engaged directly onto a needle fitting on a syringe to which it is desired to transfer injection fluid. Whilst this patent describes a satisfactory arrangement for use with a standard friction fit needle fitting such as a luer slip fitting, it does not deal with the problems associated with syringes utilizing screw thread engagement systems such as the luer lock system.

It is an object of the present invention to provide a container suitable for use with a syringe having a screw thread engagement fitting to facilitate more secure, easier and more convenient transfer of an injection solution to a syringe which has a screw thread engagement fitting than has hitherto been possible.

DESCRIPTION OF THE INVENTION

According to the present invention, there is provided a liquid containing thermoplastic unit dose container which comprises a body portion, a neck portion and an outlet opening at the end of the neck portion which is sealed by a non resealable cap, wherein the outside wall of the neck portion comprises a thread engagement portion which is located at or proximate the outermost edge of the neck portion so that after removal of the cap the thread engagement portion is adapted to engage within an inwardly facing screw thread channel at the end of a syringe, thus enabling sealing connection of the container to the said syringe so that liquid within the container may be directly transferred from the container to the syringe.

The cap is preferably attached to the outlet opening along a weakened section so that it may be readily detached by a rocking or twisting action. Preferably, the outside wall of the container neck comprises a thread engagement portion and a non engagement portion. In such an embodiment, the thread engagement portion has a cross sectional diameter greater than the distance between the top of the thread on opposite sides of the syringe fitting and is adapted to engage in the screw thread channel of the syringe to facilitate connection.

The diameter of the non engagement portion is equal to or preferably smaller than the distance between the top of the thread on opposite sides of the syringe fitting so that it effectively clears the thread when the neck is drawn onto the screw thread of the syringe by the engagement of the thread engagement portion in the thread channel.

The thread engagement portion can be of any shape that will engage within the screw thread channel of the syringe fitting. Most preferably, the thread engagement portion of the neck is located at the edge of the outlet opening and comprises a shoulder shaped to fit within the screw thread channel of the syringe fitting. One example of a particular embodiment of the invention is a container having a cylindrical neck portion (being the non engagement portion) with a peripheral shoulder at the edge of the outlet opening forming the engagement portion. In other words, it is possible to form the container with parallel sides. If the screw thread fitting comprises a central cone such as in the luer lock fitting, it is preferred that these sides be sized to seal against the luer cone. Alternatively, the container may have an inverted truncated cone neck portion with the leading edge thereof being formed to engage with the thread on a syringe fitting (the thread engagement portion) and the trailing section of the truncated cone forming the non engagement portion of the neck.

The container of the present invention is particularly useful for use with syringes having screw thread engagement fittings such as the "luer lock" fitting. The luer lock fitting comprises a central male cone, an outer peripheral wall and a bottom wall. The outside wall of the cone, the bottom wall and the inside of the peripheral wall together define an annular channel. On the inside of the peripheral wall there is provided a screw thread.

When used in conjunction with a syringe having a fitting like that of the luer lock, it is necessary that the outlet opening of the container be large enough to accommodate the central male cone on the syringe.

Thus according to one embodiment of the invention, the diameter of the neck portion is equal to or slightly smaller than the corresponding outside diameter of the cone on the syringe fitting at at least one portion of the container neck. As the container of the invention is of a thermoplastic material, it is capable of slight deformation and the diameter of the neck portion in at least one position is most preferably slightly smaller than the outside diameter of the syringe so to sealingly abut against the cone at that point or points.

Where sealing engagement is facilitated in this manner, it is not necessary that the engagement portion of the container neck also provide a seal with the fitting although this is desirable. It is however very important that sealing engagement occur either between the engagement portion of the neck and the peripheral wall of the fitting or alternatively between a portion of the inside of the container neck and the central make cone. If there is no sealing connection, it is possible for the intrusion of unsterile air into the container and this may lead to contamination of the container contents of the syringe.

Sealing between the container and the syringe fitting is also enhanced if the engagement portion of the neck is slightly greater in cross sectional diameter than the internal diameter of the annular channel. This means that upon engagement of the container with the syringe, the engagement portion slightly deforms and sealingly abuts against the inside of the peripheral wall.

The body of the container may be of any shape. However, it is preferred that the top of the body be formed hexagonally. The hexagonal form makes it easier to connect the syringe to the container as it strengthens the container in such a way that it can stand radial and axial strains better. The hexagonal upper part of the body is then further strengthened by one yoke on each side. The yokes also reduce the risk of the containers being punctured when they are being produced.

In use, the transfer of injection solution held within a container made in accordance with the invention is effected in the following way.

First, the non resealable container cap is removed by a rocking or twisting action and separates from the container along the weakened portion adjacent the outlet opening. The container is held in an upright position and the syringe into which it is intended to transfer the solution is placed so that the screw thread engagement fitting aligns with the outlet opening. The plunger in the syringe should be fully inserted. The container is then sealingly engaged with the syringe fitting by rotating the syringe and container with respect to each other until the container has completely engaged with the screw thread on the syringe. When so connected, the contents of the container may be conveniently withdrawn into the syringe by the rearward action of the plunger in the syringe body and if necessary, assistance in this fluid transfer may be given by partial deformation of the outside walls of the container.

The invention is further described below with reference to preferred embodiments of the invention shown in the accompanying drawings wherein.

Figure 1:
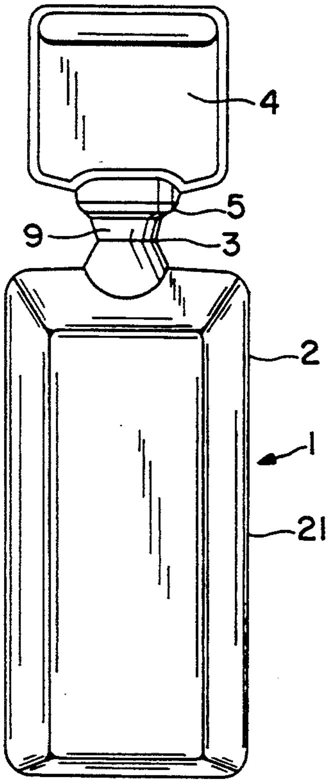
FIG. 1 illustrates a front view of a unit dose container made in accordance with the invention sealed by a non resealable cap.
Figure 2:
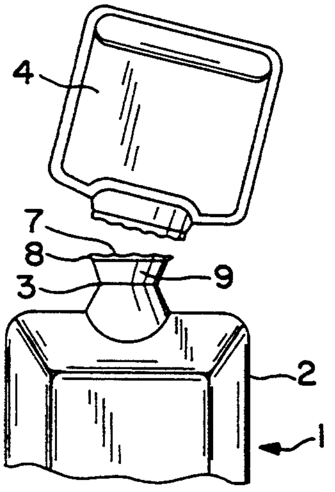
FIG. 2 illustrates the top part of the unit dose container of FIG. 1 with the cap removed from the outlet opening.

In FIG. 1 there is shown a container 1 of thermoplastic material which can be readily deformed. Suitable materials for the manufacture of such containers are well known in the art but include polyethylene and polypropylene. The container 1 comprises a body portion 2 and a neck portion 3. At the end of the neck portion, there is provided a non resealable cap 4 connected to the end of neck 3 along weakened line 5. Neck portion 3 is in the form of an outwardly widening truncated cone and this feature is easier to identify in FIG. 2.

Figure 3:
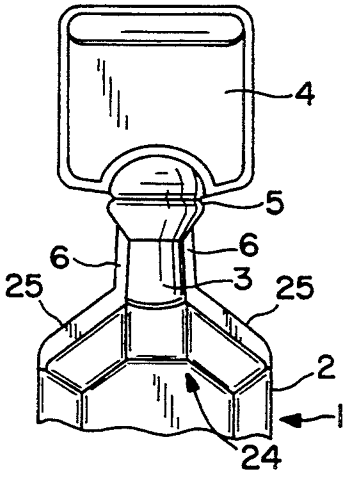
FIG. 3 illustrates the top portion of an alternative embodiment of the invention.

In FIG. 3 there is shown an alternative embodiment of the invention wherein the top 24 of the body is formed hexagonally and the body is strengthened by one yoke 25 on each side.

FIG. 3 also shows a cylindrical neck portion having a non-varying cross-sectional diameter.

The non resealable cap 4 may be removed from neck portion 3 by a rocking or twisting action and separates from the neck portion 3 along weakened line 5. After removal of the non resealable cap, there is revealed an outlet opening 7 at the end of neck portion 3 through which, liquid contained in container 1 may pass.

Figure 4:
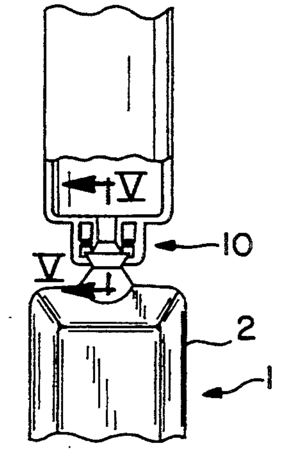
FIG. 4 illustrates the unit dose container of FIG. 2 with a syringe connected to the outlet opening thereof.
Figure 5:
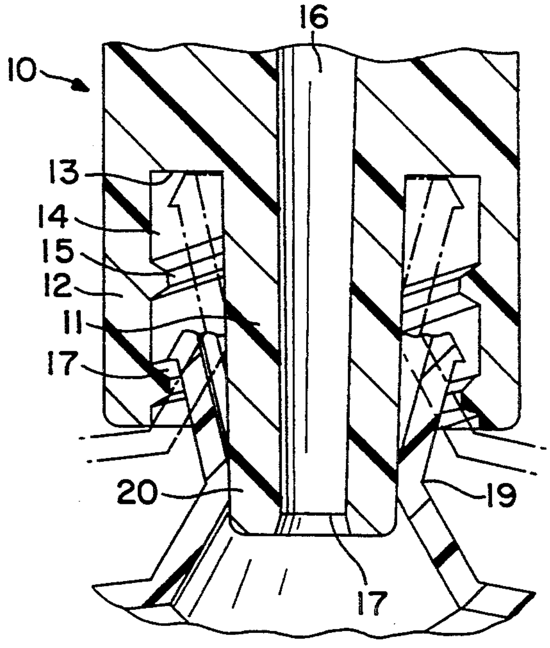
FIG. 5 is an exploded view of the connection between the outlet opening and the syringe fitting as illustrated in FIG. 4.

Neck portion 3 comprises a thread engagement portion being the shoulder 8 located about the peripheral edge of outlet 7. The neck portion also comprises a non engagement portion 9 of reduced cross sectional diameter. FIGS. 4 and 5 show the connection of such a container to a syringe so to facilitate transfer of the liquid contained in the container to the syringe. These figures illustrate a syringe having a luer lock needle fitting 10. This fitting has a central male cone 11, an outer peripheral wall 12 and a bottom wall 13. These walls form the boundary of an annular channel 14. A screw thread 15 is provided on the inside wall of peripheral wall 12. The central luer cone 11 is provided with a transfer channel 16 which is open at its outer most end 17.

In FIG. 3, the engagement portion has a less sharply defined edge. This shoulder is adapted to engage with the screw thread fitting of the syringe but may require continued application of force during connection with the screw thread to ensure engagement. The neck is strengthened by yokes 6 and the top of the package is hexagonally formed.

The container 1 is adapted to engage with the luer lock fitting 10 as follows. After the non resealable cap 4 is removed from container 1, it is held in an upright position and the syringe fitting 10 is located adjacent to the outlet opening 7 of container 1 whereby central luer cone 11 is inserted into the outlet opening 7. By relative rotation of the container with respect to the syringe fitting, thread engagement shoulder 8 on neck 3 is caused to engage with thread 15. To assist in initial engagement, the syringe fitting may be pushed slightly down into the outlet opening 7. Once the thread "takes", shoulder 8 fits behind the thread 15 and abuts against the underside 17 of the thread and the inside of peripheral wall 12. The non engagement portion 9 of neck 3 is of narrower cross section so that it does not interfere with the thread 15 but can move freely into channel 14 whilst the container is screwed onto the syringe fitting.

The internal diameter of neck 3 at point 19 is slightly smaller than the outside cross sectional diameter of cone 11. As can be seen in FIG. 5, this ensures sealing engagement between the components at the area generally designated by the numeral 20. The extent of the sealing at 20 improves as the container is screwed onto the luer lock fitting as in a standard luer cone, the side wall of the cone is slightly inclined with the base of the cone being of slightly increased diameter than the top of the cone.

Accordingly, as container 1 is screwed onto the screw thread fitting 10, that portion of the neck indicated at position 19 is forced outwardly to increase the internal diameter of the neck at this position. This causes stresses in the neck resulting in closer and tighter abutment of portion 19 against the outside wall of cone 11 as the container is screwed onto the needle fitting.

In FIG. 5, there is also shown in hatch lines the position of the container once fully screwed onto the needle fitting. In this position, the top of the outlet opening 7 abuts against the base 13 of the needle fitting to further ensure sealing engagement of the container onto the needle fitting.

Once the container has been fully secured onto the needle fitting, transfer of the injectable solution in the container is easily effected by the rearward action of the plunger in the syringe body. Most preferably, the container side walls are flexible enough so that the container can partially collapse in the drawing out of the injection solution. Transfer of the solution can be assisted by squeezing the outside walls 21 of the container.

The container of the present invention can be filled with a solution of any drug which is suitable for injection but is particularly advantageous for use with aqueous solutions of autoclavable local anaesthetics such as lidocaine, prilocaine, mepivocaine, bupivocaine, etidocaine or other drugs which are used under conditions where the demands for easy handling and sterility are especially high.

Finally, it is to be understood that various alterations, modifications and/or additions may be introduced into constructions and parts previously described without departing from the spirit or ambit of the invention as defined in the following claims.

We claim:

1. A liquid drug-containing thermoplastic unit dose container for engaging and transferring liquid to a syringe of a standard size appropriate for administering the particular drug, the syringe being of the type which has a central projecting cone, an outer peripheral wall surrounding the cone, and a bottom wall together defining an annular channel, wherein the outer peripheral wall contains an inwardly facing screw thread for engaging a needle fitting; wherein said container comprises:

a body portion containing said dose;

an outlet comprising a hollow neck portion sized to receive the cone of a mating syringe and to extend up into the annular channel, the neck portion having an outwardly facing surface, an internal surface and an outermost rim; and a removable, non-resealable cap secured to said rim for sealing the outlet; wherein the outwardly facing surface of the neck portion comprises a thread engagement portion for engaging the inwardly facing screw thread of the mating syringe, such that the cap may be removed and the syringe screwed onto the container neck portion, and wherein the neck portion includes means for providing a seal between the container and the syringe cone, when the syringe is screwed onto the container, so that liquid may be directly transferred from the container to the syringe.

2. A container as defined in claim 1, wherein a portion of the internal surface of the neck portion has a diameter smaller than at least part of the outside surface of the cone and is deformable, and is positioned to contact the cone when the syringe is screwed onto the neck portion, thereby constituting the means for providing a seal between the container and syringe cone.

3. A container as defined in claim 2, wherein the neck is in the shape of an inverted truncated cone, decreasing from a maximum diameter at the rim to a minimum diameter portion, and wherein the neck is sized and shaped so as to contact the syringe cone only at the minimum diameter portion.

4. A container as defined in claim 3, wherein the neck includes a second truncated cone, having a minimum diameter portion facing and joining the minimum diameter portion of the inverted truncated cone, and wherein the neck is shaped so as to contact the syringe cone only at the minimum diameter portion joining the two cones.

5. A container as defined in claim 3, wherein the minimum diameter portion is cylindrical, having a constant diameter.

6. A container as defined in claim 1, for use with a syringe in which the outer peripheral wall has an inwardly facing surface, wherein the thread engagement portion comprises a shoulder on the outwardly facing surface of the neck, adjacent the rim, and has a diameter greater than the inwardly facing surface of the outer peripheral wall and is deformable, thereby constituting the means for providing a seal between the container and syringe cone.

7. A container as defined in claim 1, wherein the neck is sized and shaped so that the neck rim contacts the syringe bottom wall, when the syringe is screwed completely onto the container neck, and comprises the means for providing a seal between the container and syringe cone.

8. A container as defined in claim 1, wherein the body, in a region adjacent the neck, is hexagonal and includes a pair of opposed yokes for strengthening such region.

9. In combination a syringe and a liquid drug-containing thermoplastic unit dose container for engaging and transferring liquid to the syringe, wherein the syringe comprises a central projecting cone, an outer peripheral wall surrounding the cone, and a bottom wall together defining an annular channel, wherein the outer peripheral wall contains an inwardly facing screw thread for engaging a needle fitting; and wherein said container comprises:

a body portion containing said dose;

an outlet comprising a hollow neck portion sized to receive the cone of the syringe and to extend up into the annular channel, the neck portion having an outwardly facing surface, an internal surface, and an outermost rim; and a removable, non-resealable cap secured to said rim for sealing the outlet; wherein the outwardly facing surface of the neck portion comprises a thread engagement portion for engaging the inwardly facing screw thread of the mating syringe, such that the cap may be removed and the syringe screwed onto the container neck portion, and wherein the neck portion includes means for providing a seal between the container and the syringe cone, when the syringe is screwed onto the container, so that liquid may be directly transferred from the container to the syringe.

10. The combination defined in claim 9, wherein a portion of the internal surface of the neck portion has a diameter smaller than at least part of the outside surface of the cone and is deformable, and is positioned to contact the cone when the syringe is screwed onto the neck portion, thereby constituting the means for providing a seal between the container and syringe cone.

11. The combination defined in claim 10, wherein the neck is in the shape of an inverted truncated cone, decreasing to a minimum diameter portion, and wherein the neck is shaped so as to contact the syringe cone only at the minimum diameter portion.

12. The combination defined in claim 11, wherein the neck includes a second truncated cone, having a minimum diameter portion facing and joining the minimum diameter portion of the inverted truncated cone, and wherein the neck is shaped so as to contact the syringe cone only at the minimum diameter portion joining the two cones.

13. The combination defined in claim 11, wherein the minimum diameter portion is cylindrical, having a constant diameter.

14. The combination defined in claim 11, wherein the cone of the syringe has an outlet end and tapers in diameter toward the outlet end, such that when the syringe is screwed onto the container neck, and the cone moves further into the neck, the seal formed at the minimum diameter region increases.

15. The combination defined in claim 11, wherein the outer peripheral wall of the syringe has an inwardly facing surface, wherein the thread engagement portion comprises a shoulder on the outwardly facing surface of the neck, adjacent the rim, and has a diameter greater than the inwardly facing surface of the outer peripheral wall and is deformable, thereby constituting a means for providing an additional seal between the container and syringe.

16. The combination defined in claim 15, wherein the neck is sized and shaped so that the neck rim contacts the syringe bottom wall, when the syringe is screwed completely onto the container neck, and comprises a means for creating an additional seal between the container and syringe cone.

17. The combination defined in claim 9, wherein the outer peripheral wall of the syringe has an inwardly facing surface, wherein the thread engagement portion comprises a shoulder on the outwardly facing surface of the neck, adjacent the rim, and has a diameter greater than the inwardly facing surface of the outer peripheral wall and is deformable, thereby constituting the means for providing a seal between the container and syringe cone.

18. The combination defined in claim 9, wherein the body, in a region adjacent the neck, is hexagonal and includes a pair of opposed yokes for strengthening such region.

19. The combination defined in claim 9, wherein the neck is sized and shaped so that the neck rim contacts the syringe bottom wall, when the syringe is screwed completely onto the container neck, and comprises the means for providing a seal between the container and syringe cone.

20. A method of providing a liquid drug dose to a syringe, comprising the steps of:

providing a syringe having a central projecting cone, an outer peripheral wall surrounding the cone, and a bottom wall together defining an annular channel, wherein the outer peripheral wall contains an inwardly facing screw thread for engaging a needle fitting;

providing a liquid drug-containing thermoplastic unit dose container comprising a body portion containing said dose; an outlet comprising a hollow neck portion sized to receive the cone of the syringe and to extend up into the annular channel, the neck portion having an outwardly facing surface, an internal surface, and an outermost rim; and a removable, non-resealable cap secured to said rim for sealing the outlet; wherein the outwardly facing surface of the neck portion comprises a thread engagement portion for engaging the inwardly facing screw thread of the mating syringe, and wherein the neck portion includes means for providing a seal between the container and the syringe cone, when the syringe is screwed onto the container;

removing the cap from the container to expose the container rim;

screwing the syringe onto the container neck so as to form a seal between the container and syringe cone, and transferring liquid from the container to the syringe.

* * * * *